(12) United States Patent
Munro et al.

(10) Patent No.: US 9,164,045 B2
(45) Date of Patent: Oct. 20, 2015

(54) PHASE IMAGING

(75) Inventors: Peter Munro, Como (AU); Alessandro Olivo, London (GB); Konstantin Ignatyev, Didcot (GB); Robert Speller, Bedfordshire (GB)

(73) Assignee: UCL BUSINESS PLC, London (GB)

(*) Notice: Subject to any disclaimer, the term of this patent is extended or adjusted under 35 U.S.C. 154(b) by 149 days.

(21) Appl. No.: 14/233,050

(22) PCT Filed: Jul. 19, 2012

(86) PCT No.: PCT/GB2012/051725
§ 371 (c)(1),
(2), (4) Date: Apr. 24, 2014

(87) PCT Pub. No.: WO2013/011317
PCT Pub. Date: Jan. 24, 2013

(65) Prior Publication Data
US 2014/0233699 A1    Aug. 21, 2014

(30) Foreign Application Priority Data

Jul. 21, 2011 (GB) .................................. 1112506.9

(51) Int. Cl.
*G01N 23/04* (2006.01)
*A61B 6/00* (2006.01)

(52) U.S. Cl.
CPC .............. *G01N 23/04* (2013.01); *G01N 23/046* (2013.01); *A61B 6/4291* (2013.01); *A61B 6/484* (2013.01); *A61B 6/5205* (2013.01); *G01N 2223/419* (2013.01)

(58) Field of Classification Search
CPC .... A61B 6/4291; A61B 6/484; A61B 6/5205; A61B 6/4233; A61B 6/502; A61B 6/4441; A61B 6/4464; A61B 6/06; A61B 6/4452; A61B 6/504; A61B 6/032; A61B 6/4021; A61B 6/4035; A61B 5/14532; A61B 5/1455; A61B 5/7232; A61B 6/037; A61B 6/481; A61B 6/00; A61B 6/5217; A61B 6/4007; A61B 6/4092; A61B 6/482; A61B 6/5282; A61B 5/055; G01N 2223/419; G01N 23/04; G01N 23/046
USPC ................................................ 378/62, 37, 41
See application file for complete search history.

(56) References Cited

U.S. PATENT DOCUMENTS

| | | | | |
|---|---|---|---|---|
| 2012/0189101 | A1* | 7/2012 | Kaneko | 378/62 |
| 2012/0294421 | A1* | 11/2012 | Mukaide et al. | 378/62 |
| 2013/0010926 | A1* | 1/2013 | Tada | 378/62 |
| 2013/0129049 | A1* | 5/2013 | Ishii | 378/62 |

FOREIGN PATENT DOCUMENTS

| | | |
|---|---|---|
| GB | 2441578 | 3/2008 |
| GB | 2479328 | 10/2011 |

(Continued)

OTHER PUBLICATIONS

Peter R T Munro et al: "Design of a novel phase contrast X-ray imaging system for mammography", Nuclear Instruments & Methods in Physics Research. Section A: Accelerators, Spectrometers, Detectors, and Associated Equipment, vol. 652, No. 1, Oct. 1, 2010, pp. 824-828, XP028291763, ISSN: 0168-9002, DOI: 10.1016/J.NIMA.2010.09.083 [retrieved on Oct. 1, 2010] the whole document.

*Primary Examiner* — Irakli Kiknadze
(74) *Attorney, Agent, or Firm* — Leason Ellis LLP

(57) ABSTRACT

A method of phase imaging uses X-ray beams having edges overlapping with pixels. A phase image may be obtained from first and second images using one or more X-ray beam, the first image being measured with the first edge but not the second edge of each X-ray beam overlapping the corresponding pixel(s) and the second image being measured with the second edge but not the first edge overlapping the corresponding pixel(s). The gradient of the X-ray absorption function may be calculated and a proportional term included in the image processing to calculate a quantitative phase image.

15 Claims, 6 Drawing Sheets

(56) References Cited

FOREIGN PATENT DOCUMENTS

| WO | WO 2008/029107 | 3/2008 |
| WO | WO 2008/102654 | 8/2008 |
| WO | WO 2009/076700 | 6/2009 |
| WO | WO 2011/068230 | 6/2011 |
| WO | WO 2011/102247 | 8/2011 |

\* cited by examiner

US 9,164,045 B2

PHASE IMAGING

CROSS REFERENCE TO RELATED APPLICATIONS

The present application is a U.S. National Phase of International Patent Application PCT/GB2012/051725, filed Jul. 19, 2012, which claims priority to Great Britain Patent Application No. GB 1112506.9, filed Jul. 21, 2011, each of which is incorporated herein by reference in its entirety.

FIELD OF INVENTION

The invention relates to an apparatus and method for phase imaging.

RELATED ART

Conventional X-ray imaging systems are based on absorption of X-rays, and generate image contrast based on differences in absorption across an imaged object.

Phase contrast X-ray imaging makes use of the variable phase shift based on the differences in the speed of X-rays in an imaged object. Until recently, phase contrast imaging required very high powered X-ray beams such as those produced by synchrotrons which also produce high quality X-ray beams.

Phase contrast X-ray imaging is described in general terms in a review article by R Lewis, "Medical phase contrast x-ray imaging: current status and future prospects", Phys. Med. Biol. volume 49 (2004) pages 3573 to 3583.

A key point in favour of phase contrast X-ray imaging is that the term responsible for phase changes (the difference from unity of the real part of the refractive index) is typically of the order of 1000 times larger than the part responsible for absorption (imaginary part of the refractive index). This means that phase contrast imaging can have dramatically improved sensitivity.

A recent proposal, in WO 2008/029107, proposes carrying out phase-contrast imaging using a method that can work with conventional X-ray sources. In this approach, typically a pair of masks are used, one between the detector and the sample to create one or more X-ray beams, and one to mask part of the detector pixels. Alternatively, a single mask or a collimator can be used to exploit the same effect. The masks are aligned to detector pixels so that the X-rays overlap the effective edge of individual detector pixels. The method can deliver short acquisition times.

The method of WO 2008/029107 will be referred to as coded aperture X-ray phase contrast imaging (CAXPCI).

However, the method proposed in WO 2008/029107 does not deliver quantitative phase imaging, i.e. the images produced do not have image intensities proportional only to the phase shift due to the real part of the refractive index across the image sample.

SUMMARY OF INVENTION

According to the invention there is provided a method of phase imaging according to claim 1.

By using the method of the invention, with two images, the method proposed in WO 2008/029107 is adapted to produce a true phase image and not a phase contrast image. In the phase contrast image of WO 2008/029107 the contrast in the image produced is in fact due to a combination of the phase shift (due to the real part of the refractive index) and the absorption (due to imaginary part of the refractive index). In the image produced by the present method, there is provided a direct image of the phase shift due to the real part of the refractive index.

The method proposed in claim 1 is only exact in the case that the absorption is constant over the length scale of a pixel. In preferred arrangements, the method further includes calculating the gradient of the absorption function across the pixels, and adding a correction term to each output pixel to correct for this gradient. In other words, a linear approximation to the change in the absorption function is made and used to obtain a more precise quantitative phase image. If this is not done then the method yields approximate results in which the validity of the approximation depends on the uniformity of the absorption function.

The inventors have found that this method is very robust. In many cases, adding additional terms to image processing algorithms simply causes extra complexity and introduces artifacts. In contrast, the inventors have found that the additional term to correct for the gradient of the absorption function is robust and provides good results over a wide range of situations.

In a further preferred arrangement, the method includes moving the sample relative to the grating or gratings by one or more predetermined steps. Typical step sizes will be smaller than the pixel size. In this way, additional data may be collected which can be used for gradient extraction purposes and/or to reduce the effective pixel size, using dithering.

In another aspect, there is provided a method of phase imaging, comprising:
  providing a source of X-rays;
  directing the source of X-rays to define at least one X-ray beam with opposed first and second edges;
  passing the at least one X-ray beam through a sample region of a sample onto an X-ray detector having pixels or rows of pixels corresponding to the at least one X-ray beam;
  measuring in a first configuration where the first edge but not the second edge of each X-ray beam overlaps the corresponding pixel or row of pixels in the X-ray detector to obtain a first X-ray image; and
  obtaining a phase image by:
  calculating the gradient of the X-ray absorption function and
  combining the first X-ray image with a term proportional to the gradient of the absorption function to calculate a quantitative phase image.

BRIEF DESCRIPTION OF DRAWINGS

For a better understanding of the invention, embodiments will now be described, purely by way of example, with reference to the accompanying drawings, in which.

DETAILED DESCRIPTION

The method is a development of the CAXPI method presented in WO 2008/029107.

Figure 1:
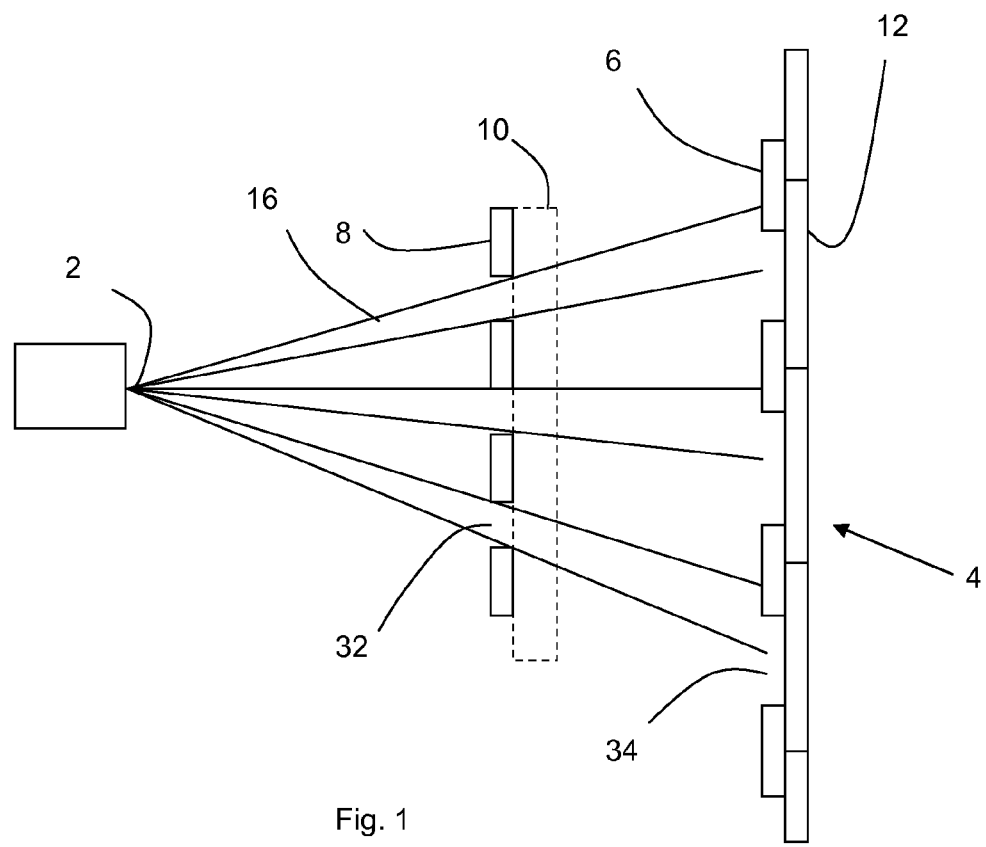
FIG. 1 is an illustration of a first embodiment of a method according to the invention.
Figure 2:
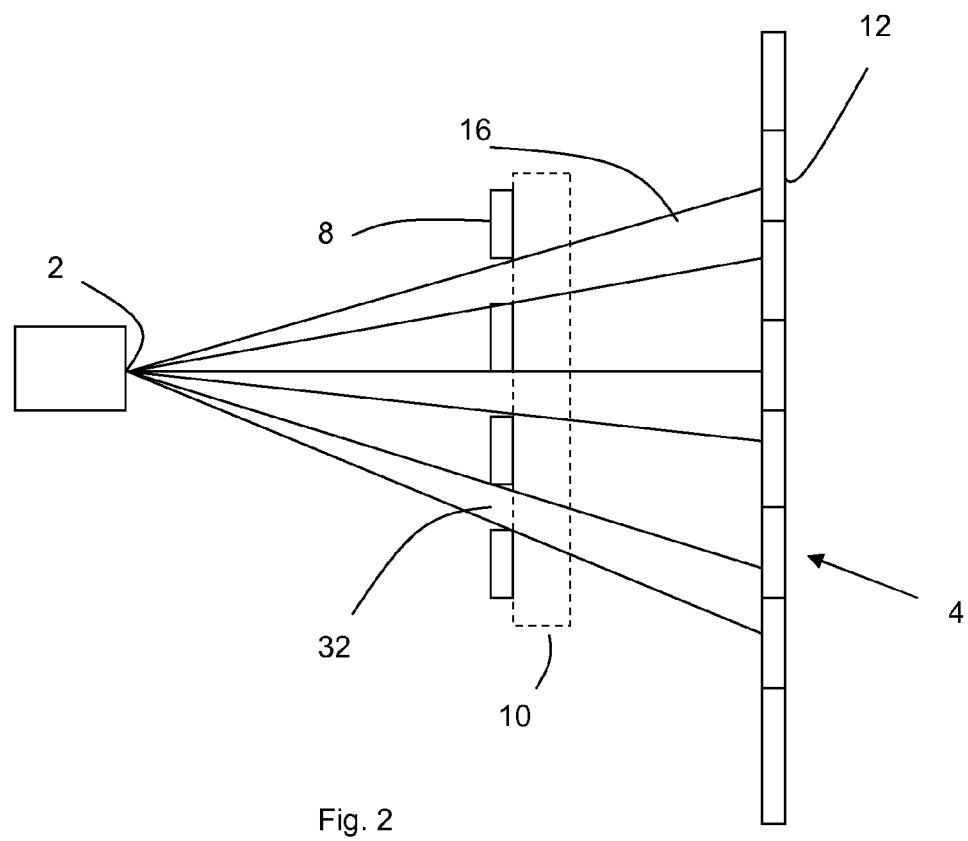
FIG. 2 is an illustration of a second embodiment of a method according to the invention.

One arrangement for such imaging is generally presented in FIGS. 1 and 2. In this arrangement, a source of X-rays 2 is passed through a sample mask 8 which has a plurality of apertures 32 which generates a corresponding plurality of X-ray beams 16. The beams 16 are aligned with pixels 12 of a detector 4. In the arrangement shown in FIG. 1, a detector mask 6 with apertures 34 is provided to delimit edges of the pixels.

A sample 10 is shown in the apparatus on the far side of the sample mask 8 from the source 2.

In another arrangement, a sample mask 8 containing a single aperture is paired with a detector mask 6 also containing a single aperture. In this arrangement a single X-ray beam, in contrast to a plurality of beams, is employed and the sample 10 is scanned through the beam.

The refractive index of the sample 10, n, may be generally expressed as a complex number, $n=1-\delta+i\beta$ where $\delta$ represents the decrement of the real part and $\beta$ is the imaginary part.

The transparency function T of an object extending in the x- and y-directions with light incident on the object in the z direction may be represented as $$T(x,y)=\exp(-i\phi(x,y)-\mu(x,y))$$

The real part $\mu$ represents absorption in the object and the imaginary part $\phi$ the phase shift of the transparency function. $\mu$ is referred to as the absorption function and $\phi$ as the phase function. In general, what needs to be measured for phase imaging is the gradient of the phase function.

Note that in FIG. 1 the apertures 32 34 in both masks extend out of the paper in the y direction—they are accordingly slits.

Although FIG. 1 illustrates an approach using a detector mask 6 the inventors have realised that the key to the present method is the measurement of two images, which will be referred to as the I+ and I− images. Taking the direction across the sample as x, the important thing is that the "lower" edge of the x-ray beam but not the "upper" edge is in the pixel for one image, and the "upper" edge of the x-ray beam but not the "lower" edge is in the pixel for the other image. By "upper" is meant the edge of the beam with highest x, and by "lower" is meant the edge of the beam with lowest x.

Figure 6:
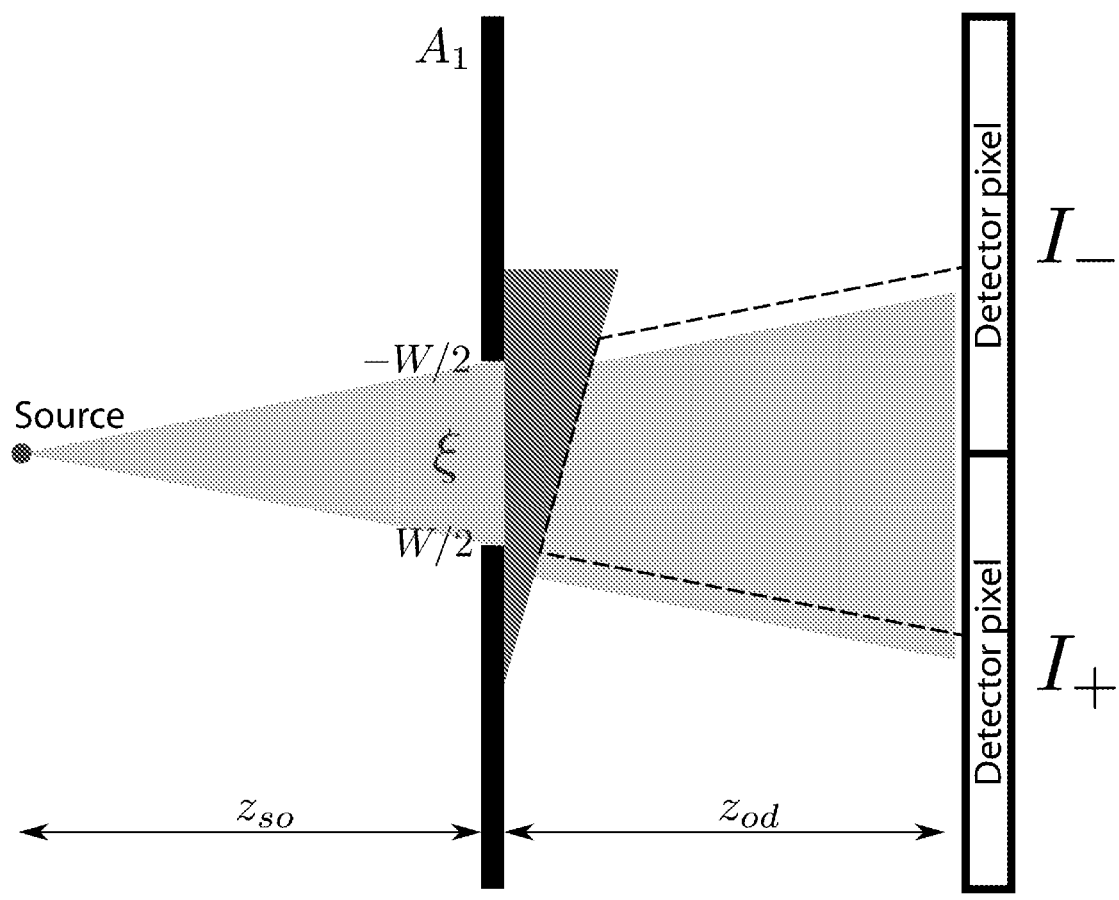

Although this may be achieved using a detector mask, it is also possible to obtain this situation as illustrated in FIG. 2 in which adjacent pixels are in the I+ and I− configurations as is shown in FIG. 6. Thus, in the configuration shown in FIG. 2, both I+ and I− images may be taken at the same time, as long as the correct pixels are assigned to the correct image. This also maximises the use of the x-ray beams and hence minimises the time taken to capture images and the dose delivered to the sample.

Although the arrangement of FIG. 2 uses all the rows of pixels, it is also possible to have the beams 16 more widely spaced so that there are pixels between the pixels capturing the I+ and I− images which are not impinged upon by any beam and hence which will not detect any photons when capturing the image. Although this reduces the efficiency of image capture, since the black pixels are essentially unused, it does give rise to an advantage in that it makes it easier to identify the pixels capturing the I+ and I− images since they are clearly shown as the pixels which are not black. In general however, the use of such gaps is not preferred since in most circumstances efficient use of X-rays is more important to reduce image capture time.

An equivalent set up is to use only a single beam and a detector mask with a single aperture and to scan the object by moving the object.

Figure 3:
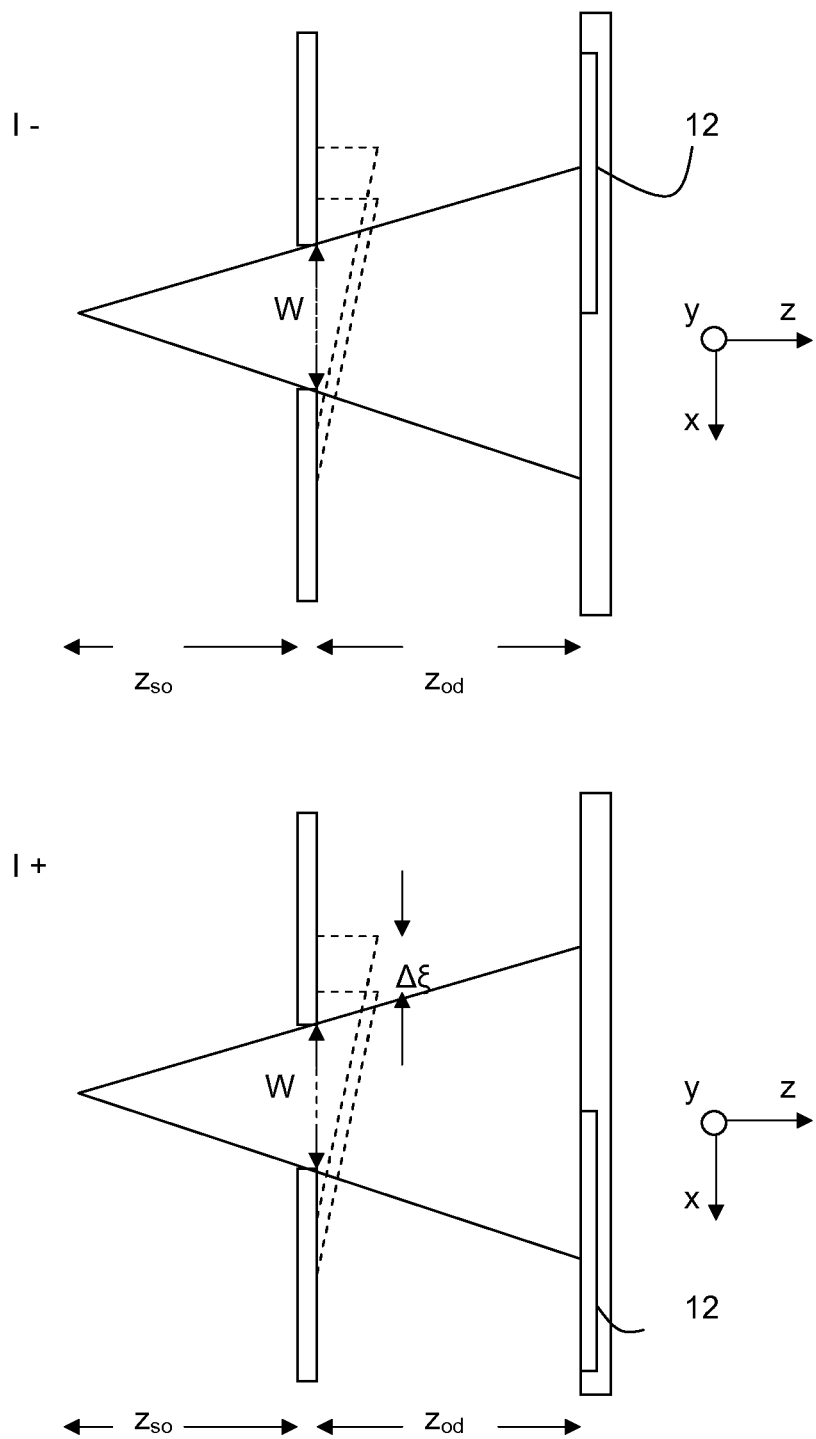
FIGS. 3 and 6 are illustrations of the mathematical quantities used in the formulae presented.

For simplicity and without loss of generality, while deriving the equations for quantitative imaging we consider the latter case, a single pair of coded apertures as demonstrated in FIG. 3.

Quantitative imaging is performed by imaging the same object using two complementary positions. Both configurations are set to an illuminated pixel fraction, IPF, of 0.5, yet will result in inverted contrasts. It should be noted, however, that using an IPF of 0.5 is not necessary and that other IPF values can be used. For the prism like object depicted in FIG. 3, the configuration denoted by I− will result in a detected signal which is lower than the flat field whilst the I+ configuration will result in a detected signal which is greater than the flat field. For simplicity's sake we will derive the equations of the quantitative method by assuming a monochromatic point source. Within the paraxial (i.e., small angle) approximation, a point source results in an X-ray intensity which is uniform in the y direction of FIG. 3. Since we assume that the imaging system and object are uniform in the y direction, we consider only variations of intensity in the x direction. If the complex amplitude of X-rays incident upon A2 is given by U(x) then, assuming a pixel of height P, I− and I+ are given by:

$$I_-=\int_0^P \int_{-MW}^0 |U(x)|^2 dxdy \quad I_+=\int_0^P \int_0^{MW} |U(x)|^2 dxdy \qquad \text{Equation 1}$$

where M is the system magnification.

Note that there are two approaches to taking measurements. In one approach, the object is scanned (moved) relative to the imaging system. In the other, the entire object is imaged simultaneously in parallel using different pixels aligned with different X-ray beams. In this latter case, the step size is equivalent to the size of the pixels. The two approaches are mathematically equivalent. However, for generality, the measurements of the two images I+ and I− are assumed to be known for the positions (represented by variable $\xi$) at $-\Delta\xi$, 0 and $\Delta\xi$ with step size $\Delta\xi$ where this can be either the scanning step size of pixel size. It is also possible to perform quantitative imaging using images I+ and I− at two positions 0 and $\Delta\xi$ Firstly, the gradient of the absorption function $\mu$ as a function of object position $\xi$ is calculated at the zero position $\xi_o$ using a step size $\Delta\xi$:

$$\left.\frac{\partial\mu}{\partial\xi}\right|^{\xi_0} = \frac{1}{4\Delta\xi}\log\left(\frac{(I_+ + I_-)|^{\xi_i=\Delta\xi}}{(I_+ + I_-)|^{\xi_i=-\Delta\xi}}\right) \qquad \text{Equation 2a}$$

In some configurations I+ and I− may be known at two locations only, namely at 0 and $\Delta\xi$. In this case the gradient of the absorption function may be found as:

$$\left.\frac{\partial\mu}{\partial\xi}\right|^{\xi_0} = \frac{1}{2\Delta\xi}\log\left(\frac{(I_+ + I_-)|^{\xi_i=\Delta\xi}}{(I_+ + I_-)|^{\xi_i=0}}\right)\left.\frac{\partial\mu}{\partial\xi}\right|^{\xi_0} \qquad \text{Equation 2b}$$

will be referred to as the gradient of the absorption function below.

The gradient of the phase function is then determined by the formula:

$$(1/k)\left.\frac{\partial\phi}{\partial\xi}\right|^{\xi_0} = \frac{-\log\left[\frac{I_+ - I_-}{I_+ + I_-}\right|^{\xi_0} \sinh\left(\left.\frac{\partial\mu}{\partial\xi}\right|^{\xi_0} W\right) + \cosh\left(\left.\frac{\partial\mu}{\partial\xi}\right|^{\xi_0} W\right)\right]}{2\left.\frac{\partial\mu}{\partial\xi}\right|^{\xi_0} \frac{(z_{so}+z_{od})}{z_{so}z_{od}}} \qquad \text{Equation 3}$$

which as will be noted includes the value calculated above.

In this formula, k is the wavenumber ($2\pi/\lambda$, where $\lambda$ is the wavelength), W is the width of the slit in the sample mask, $z_{so}$ is the distance between the source and the sample mask, and $z_{od}$ is the distance between the sample mask and the detector mask, or the detector in the case that the detector mask is absent.

More details about the derivation of these formulae are presented in Appendix A.

In many practical situations the sin h and cos h functions can be approximated to result in the formula:

$$(1/k)\frac{\partial \phi}{\partial \xi}\Big|_{\xi_0} = -\left[\frac{I_+ - I_-}{I_+ + I_-}\Big|_{\xi_0} + \frac{1}{2}\frac{\partial \mu}{\partial \xi}\Big|_{\xi_0} W\right]\frac{W(z_{so} + z_{od})}{2z_{so}z_{od}} \quad \text{Equation 4}$$

In the case where the gradient of the absorption function can be considered to be zero, the equation can be further simplified.

$$(1/k)\frac{\partial \phi}{\partial \xi}\Big|_{\xi_0} = -\frac{I_+ - I_-}{I_+ + I_-}\Big|_{\xi_0} \frac{W(z_{so} + z_{od})}{2z_{so}z_{od}} \quad \text{Equation 5}$$

In the case where a source other than a synchrotron or micro-focal source is used, Equation 5 may be employed for an absorption function with a non-zero or zero gradient. In such a case, the parameter W in Equation 5 is replaced by the full-width at half-maximum (FWHM) of the X-ray beams incident upon the detector 4, divided by the natural logarithm of 2, ie, FWHM/log(2). The FWHM can be calculated or measured experimentally and is determined by W and the width of the X-ray focal spot.

When a polychromatic source is employed, the gradient of the phase function is necessarily averaged over the wavelengths present in the spectrum. In particular, the gradient of the phase function is formed by a weighted average as:

$$\frac{1}{k}\frac{\partial \phi}{\partial \xi}\Big|_{\xi_0} = \int \frac{1}{k}\frac{\partial \phi}{\partial \xi}(E)\Big|_{\xi_0} \text{weight}(E)dE$$

where E refers to photon energy, the integral is taken over the spectrum of photon energies emitted by the source and the introduced function, weight (E), is defined as:

$$\text{weight}(E) = \frac{\exp(-\mu(E))EN(E)}{\int \exp(-\mu(E'))E'N(E')dE'}$$

where N(E) is the mean number of photons with energy E emitted by the source per unit of time and the integral is again taken over the spectrum of energies emitted by the source.

The application of these formulae to real measurement situations will now be discussed. Note however that those skilled in the art will realise that for some imaging applications the constants in these equations (e.g. 1/k) are not required. Thus, where we refer to "using" a formula or "using" an equation the use of the equation with different constants to those presented here is explicitly included.

Turning to the imaging arrangement depicted in FIG. 2, the I+ and I− images are captured using alternate rows of pixels in the x-direction for the I+ and I− images.

In the first approximation to the phase image, Equation 5 is used to calculate the phase image (the left hand side of equation 5) corresponding to an effective pixel centered on the edge shared by the corresponding pixels in the I+ and I− images. This is an exact phase image in the case that there is no absorption gradient. Although there will in general always be some absorption gradient, this absorption gradient may be small and in such cases this image will be a good approximation of the phase image.

Importantly, unlike the images using the method of WO 2008/029107 which correspond to a single image, either the I+ or I− images, the image calculated using equation 5 is a true phase image which does not include any contribution from absorption.

In a preferred, quantitative approach, the gradient of the phase function is calculated using equation 2 at every pixel position. The step size will correspond to the size of the pixels. Thus, the values at adjacent pixels are used to estimate the change in the transparency function and hence as an approximation to the gradient of the phase function.

These values are then used in equation 3 to calculate the quantitative phase image. The output is a true quantitative value.

In appropriate cases, the approximation of equation 4 may be used instead of equation 3 to calculate the phase image.

The approach may also use additional steps of moving the sample in the x direction, i.e. perpendicularly to the X-ray beam, by a predetermined increment ($\Delta\xi$) and the measurements repeated. The movement by the predetermined increment and the measurements may be repeated a number of times.

Another reason for moving the sample is that the pixel size of suitable detectors may be larger than the size of the increment. For example, the inventors have measured using a detector with pixels on an 85 µm pitch but using an increment of 20 µm. In this way, it is possible to calculate the image with an effective pixel size of 20 µm.

Experimental results were captured to verify the approach. In order to check the mathematics, an experimental verification of the phase extraction technique was performed at the SYRMEP bending magnet beamline at Elettra, the synchrotron radiation facility in operation in Trieste, Italy.

A channel-cut Si (1,1,1) crystal monochromatizes the beam to nominal photon energy 20 keV with a fractional bandwidth of 0.2%. A photon counting, linear array silicon microstrip detector known as PICASSO was employed. The detector works in the so-called "edge-on" configuration and provides an array of 2368 pixels 50 µm wide and 300 µm high. A useful property of the PICASSO detector is that it exhibits negligible pixel cross talk.

Figure 4:
FIGS. 4 to 5 and 7 are experimental results.
Figure 4:
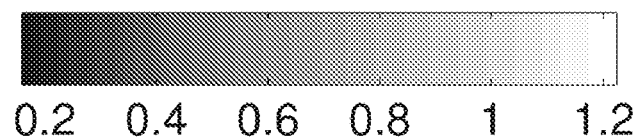
Figure 4:
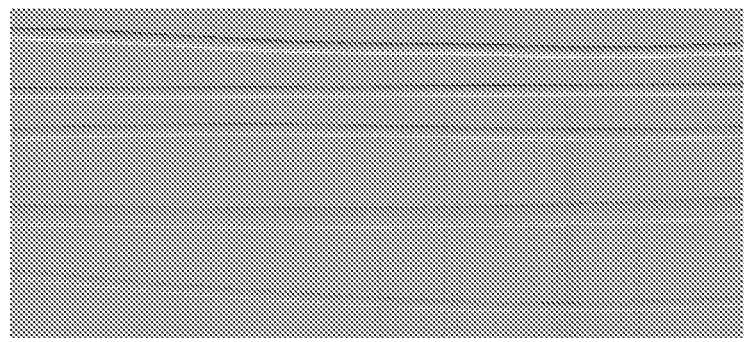
Figure 4:
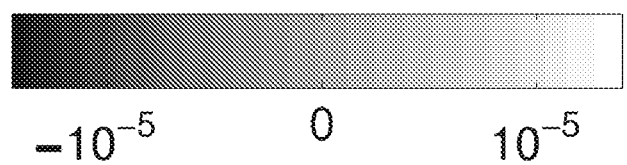

Results of the absorption (top) and phase image (bottom) are illustrated in FIG. 4. The sample is five filaments of variable diameter as follows (from top to bottom):

| Wire Material | Nominal Diameter µm | Estimated Diameter µm | $\delta/10^{-7}$ (at 20 keV) | $\beta/10^{-10}$ (at 20 keV) |
|---|---|---|---|---|
| Titanium | 250 ± 10% | 260 ± 10% | 21.9 | 346 |
| Sapphire | 250 ± 20% | 250 ± 10% | 20.3 | 39.9 |
| Aluminium | 250 ± 10% | 260 ± 10% | 13.5 | 42.2 |
| PEEK | 450 ± 20% | 480 ± 10% | 7.15 | 2.74 |
| PEEK | 200 ± 20% | 210 ± 10% | 7.15 | 2.74 |

Note the improved visibility of the phase image for the lower lines.

Figure 5:
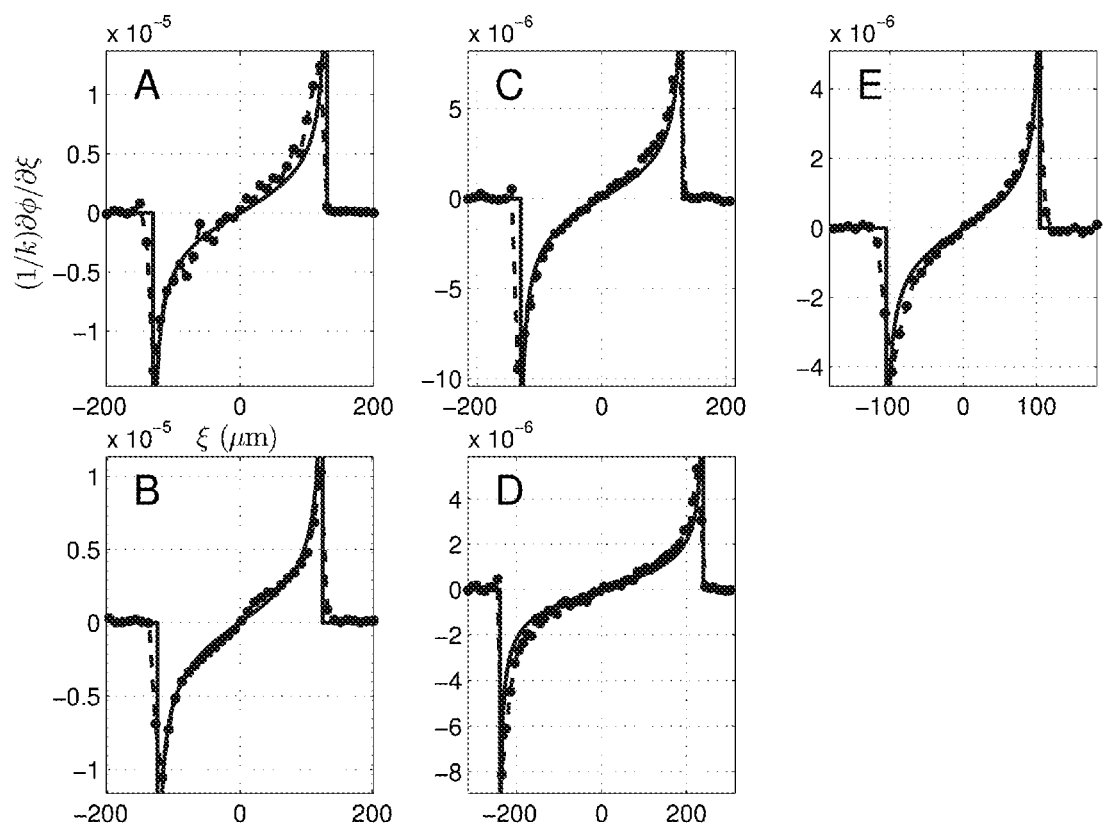

Further, the calculated profile of the gradient of the phase function was compared with the measured results. Excellent quantitative agreement was found. See FIG. 5, in which the solid line is the calculated value and the dots experimental values.

Figure 7:
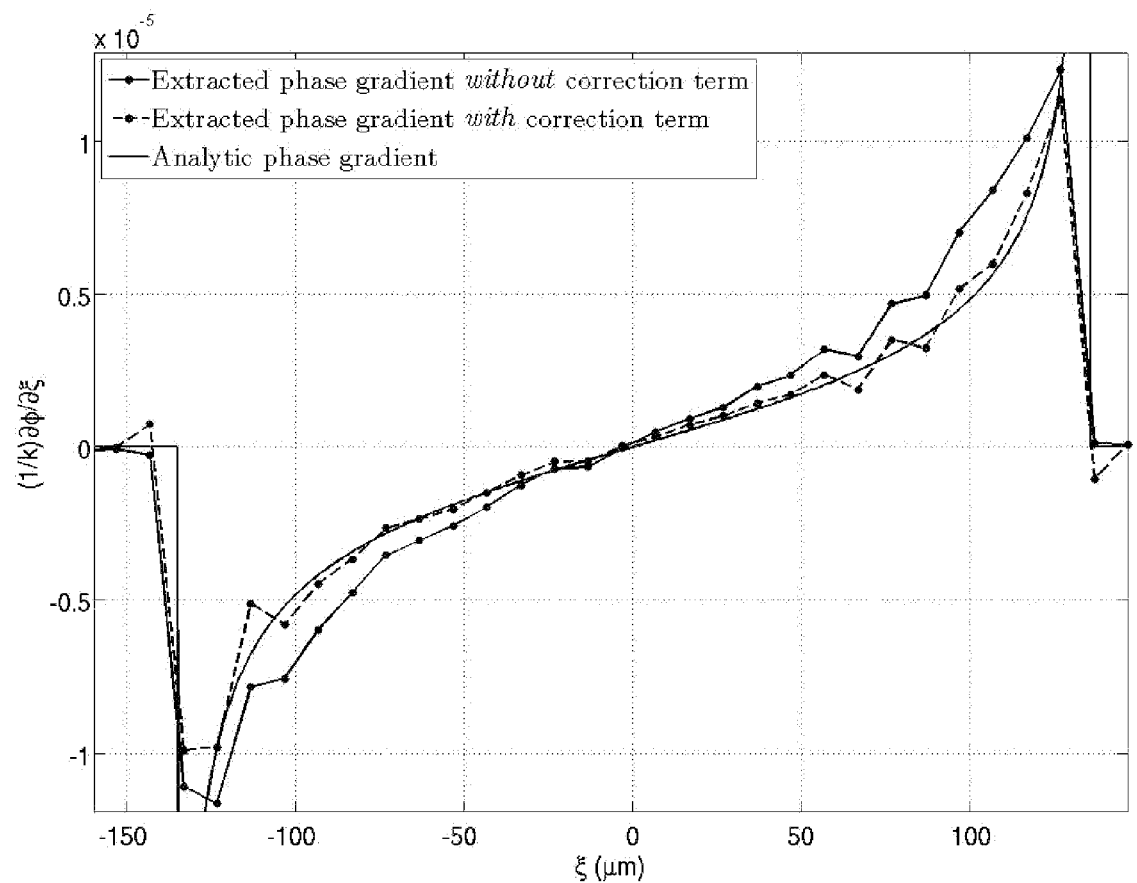

FIG. 7 shows the experimental results for the Titanium sample for the cases where the correction is included and where it is not included. The case where the correction term is included is closer to the actual value of the gradient of the phase function.

A number of alternative arrangements to carry out the same method are possible. Firstly, instead of a sample mask to create a plurality of beams, a single collimated X-ray beam may be used. In this case, either the sample or the beam may be moved to scan the sample.

Similarly, it is possible to use either the edges of the pixels or a mask.

Figure 8:
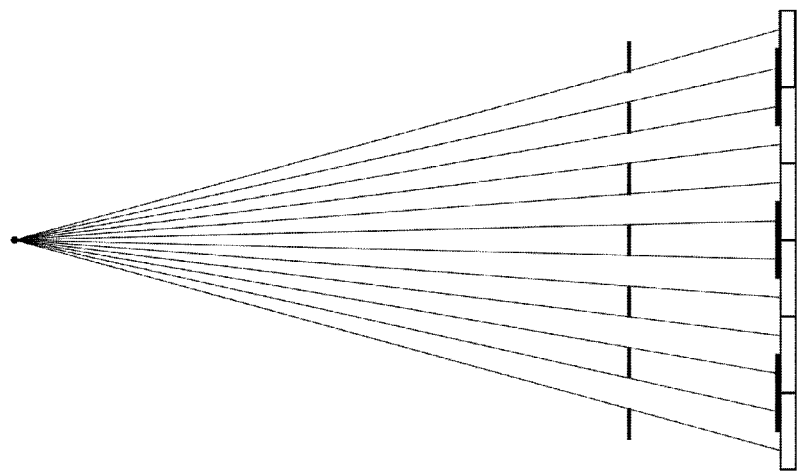
FIG. 8 illustrates a third embodiment of the invention.

FIG. 8 illustrates an alternative arrangement. In the embodiments described above, the first and second images are acquired sequentially. In the arrangement of FIG. 8, both first X-ray beams 80 and second X-ray beams 82 are present simultaneously, alternating in the x-direction and first and second images (I– and I+) are acquired simultaneously from alternating pixels. This relies on an approximation that the gradients of the imaged object's phase and absorption functions do not vary significantly on the scale of the separation in the x-direction of the X-ray beams.

When an object with negligible absorption is imaged, a single acquisition of I– or I+ is sufficient to retrieve the gradient of the phase function as long as a simple flat field image, commonly used in digital imaging, is available. This would even be unnecessary if the intensity of the incoming beam can be estimated from the image of the low absorbing object itself. In the absence of an absorbing object, the quantity I–+I+ is constant. This is a result of energy conservation and also follows from Equation 1 and the mathematical formulation used to evaluate U(x). In this case the following equation holds:

$$I_0 = I_- + I_+ \quad \text{Equation 6}$$

where $I_0$ is sometimes referred to as the flat field and remains constant as long as no absorbing objects are imaged. Once I0 is known, I– can be obtained from $I_+$ as $I_- = I_0 - I_+$ and vice versa for any subsequent object of negligible absorption. Thus, in the case of objects of negligible absorption, only one of $I_-$ and $I_+$ in combination with $I_0$ is required to evaluate the gradient of the phase function by substitution into Equation 5 resulting in:

$$(1/k)\frac{\partial \phi}{\partial \xi}\bigg|^{\xi_0} = \left(1 - \frac{2I_+}{I_0}\bigg|^{\xi_0}\right)\frac{W(z_{so}+z_{od})}{2z_{so}z_{od}} \quad \text{Equation 7a}$$

or $$(1/k)\frac{\partial \phi}{\partial \xi}\bigg|^{\xi_0} = \left(\frac{2I_-}{I_0}\bigg|^{\xi_0} - 1\right)\frac{W(z_{so}+z_{od})}{2z_{so}z_{od}} \quad \text{Equation 7b}$$

The invention claimed is:

1. A method of phase imaging, comprising:
providing a source (2) of X-rays;
directing the source (2) of X-rays to define at least one X-ray beam with opposed first and second edges;
passing the at least one X-ray beam through a sample region of a sample onto an X-ray detector having pixels or rows of pixels corresponding to the at least one X-ray beam;
obtaining a first image in a first configuration wherein the at least one X-ray beam includes at least one first X-ray beam where the first edge but not the second edge of each first X-ray beam overlaps the corresponding pixel or row of pixels in the X-ray detector and
obtaining a second image in a second configuration wherein the at least one X-ray beam includes at least one second X-ray beam where the second edge but not the first edge of each second X-ray beam overlaps the corresponding pixel or row of pixels in the X-ray detector to obtain a second X-ray image; and
obtaining a phase image from the first and second X-ray images by taking the difference between the first and second X-ray images.

2. A method according to claim 1 wherein the X-ray absorption function is calculated by adding the first and second X-ray images.

3. A method according to claim 1 wherein the step of obtaining a phase image includes:
calculating the gradient of the X-ray absorption function and
adding the difference between the first and second X-ray images to a term proportional to the gradient of the absorption function to calculate a quantitative phase image.

4. A method according to claim 3 wherein the gradient of the X-ray absorption function is calculated from the sum of the first and second X-ray images at a plurality of position steps ($\Delta\xi$) along the x-direction.

5. A method according to claim 4, wherein the gradient of the X-ray absorption function is given by:

$$\frac{\partial \mu}{\partial \xi}\bigg|^{\xi_0} = \frac{1}{4\Delta\xi}\log\left(\frac{I_+ + I_-\,|^{\xi_i=\Delta\xi}}{I_+ + I_-\,|^{\xi_i=-\Delta\xi}}\right)$$

where $\xi_i$ is the distance along a direction perpendicular to the X-ray beam, $\xi_o$ is the location at which the gradient is determined, and $\Delta\xi$ is a step in the direction $\xi_i$.

6. A method according to claim 4, wherein the gradient of the X-ray absorption function is given by:

$$\frac{\partial \mu}{\partial \xi}\bigg|^{\xi_0} = \frac{1}{2\Delta\xi}\log\left(\frac{I_+ + I_-\,|^{\xi_i=\Delta\xi}}{I_+ + I_-\,|^{\xi_i=0}}\right)$$

where $\xi_i$ is the distance along a direction perpendicular to the X-ray beam, $\xi_o$ is the location at which the gradient is determined, and $\Delta\xi$ is a step in the direction $\xi_i$.

7. A method according to claim 1 wherein the step of obtaining the gradient of the phase function is carried out using the formula:

$$(1/k)\frac{\partial \phi}{\partial \xi}\bigg|^{\xi_0} = -\log\left[\frac{I_+ - I_-}{I_+ + I_-}\bigg|^{\xi_0}\sinh\left(\frac{\partial \mu}{\partial \xi}\bigg|^{\xi_0}W\right) + \cosh\left(\frac{\partial \mu}{\partial \xi}\bigg|^{\xi_0}W\right)\right]\frac{(z_{so}+z_{od})}{2\frac{\partial \mu}{\partial \xi}\bigg|^{\xi_0}z_{so}z_{od}}$$

where $\xi_i$ is the distance along a direction perpendicular to the direction of propagation of the X-ray beam, $\xi_o$ is the location at which the gradient is determined, k is the wavenumber $2\pi/\lambda$, where $\lambda$ is the wavelength, W is the width of the slit in the sample mask, $z_{so}$ is the distance between source and the sample mask, and $z_{od}$ is the distance between the sample mask and the detector mask, or detector in the case that the detector mask is absent, and $$\left.\frac{\partial \mu}{\partial \xi}\right|^{\xi_0}$$

is the gradient of the X-ray absorption function.

8. A method according to claim 1, wherein the source is non-monochromatic and emits a spectrum of energies E, and the gradient of the phase function represents a weighted average over the energies E given by:

$$\left.\frac{1}{k}\frac{\partial \phi}{\partial \xi}\right|^{\xi_0} = \int \left.\frac{1}{k}\frac{\partial \phi}{\partial \xi}(E)\right|^{\xi_0} \text{weight}(E) dE$$

where E refers to photon energy, the integral is taken over the spectrum of photon energies emitted by the source and the introduced function, weight (E), is defined as:

$$\text{weight}(E) = \frac{\exp(-\mu(E))EN(E)}{\int \exp(-\mu(E'))E'N(E')dE'}$$

where N(E) is the mean number of photons with energy E emitted by the source per unit of time and the integral is again taken over the spectrum of energies emitted by the source.

9. A method according to claim 1, further comprising moving the sample by a predetermined increment in a direction perpendicular to the direction of propagation of the beam of X-rays and repeating the steps of measuring in a first configuration and measuring in a second configuration.

10. A method according to claim 9, further comprising providing a detector mask comprising an array of slits in front of the X-ray detector, the slits in the detector mask corresponding to the slits in the sample mask,
wherein the detector mask is moved from the first configuration in which the detector mask masks the second edge of the corresponding X-ray beam so that the first edge of the X-ray beam is incident on the corresponding row of pixels
to the second configuration in which the detector mask masks the first edge of the corresponding X-ray beam so that the second edge of the X-ray beam is incident on the corresponding row of pixels.

11. A method according to claim 1, wherein the first and second edges of the X-ray beam are separated in the x-direction, the sample mask has an array of slits separated in the x-direction and extending in a y-direction, with the X-ray beams travelling in the z-direction, the x- y- and z-directions being perpendicular, and
each slit corresponds to one or more corresponding rows of pixels in the X-ray detector.

12. A method according to claim 1, including generating both first and the second X-ray beams simultaneously,
so that the steps of measuring in a first configuration where the first edge but not the second edge of each first X-ray beam overlaps the corresponding pixel or row of pixels in the X-ray detector to obtain a first X-ray image and measuring in a second configuration where the second edge but not the first edge of each second X-ray beam overlaps the corresponding pixel or row of pixels in the X-ray detector to obtain a second X-ray image take place simultaneously.

13. A method of phase imaging, comprising:
providing a source (2) of X-rays;
directing the source (2) of X-rays to define at least one X-ray beam with opposed first and second edges;
passing the at least one X-ray beam through a sample region of a sample onto an X-ray detector having pixels or rows of pixels corresponding to the at least one X-ray beam;
measuring in a first configuration where the first edge but not the second edge of each X-ray beam overlaps the corresponding pixel or row of pixels in the X-ray detector to obtain a first X-ray image; and
obtaining a phase image by:
calculating the gradient of the X-ray absorption function and
combining the first X-ray image with a term proportional to the gradient of the absorption function to calculate a quantitative phase image.

14. A method according to claim 13 further comprising
measuring in a second configuration where the second edge but not the first edge of each X-ray beam overlaps the corresponding pixel or row of pixels in the X-ray detector to obtain a second X-ray image; and
calculating the phase image from the first and second X-ray images by taking the difference between the first and second X-ray images.

15. A method according to claim 13, further comprising calculating the quantitative phase imaging from a flat field image and the first image.

* * * * *